United States Patent [19] [11] 4,116,899
Fanta et al. [45] Sep. 26, 1978

[54] INCREASING ABSORBENCY OF POLYMERIC COMPOSITIONS BY CURING

[75] Inventors: George F. Fanta, Peoria; William M. Doane, Morton, both of Ill.

[73] Assignee: The United States of America as represented by the Secretary of Agriculture, Washington, D.C.

[21] Appl. No.: 824,776

[22] Filed: Aug. 15, 1977

[51] Int. Cl.$^2$ .................. C08L 1/02; C08L 1/08; C08L 3/02
[52] U.S. Cl. .................. 260/17.4 GC; 260/17 R; 260/17 A; 260/17.4 R; 260/17.4 CL; 260/17.4 ST; 260/881; 260/898
[58] Field of Search .......... 260/17 R, 17 A, 17.4 GC

[56] References Cited

U.S. PATENT DOCUMENTS

| 3,997,484 | 12/1976 | Weaver et al. | 260/17.4 |
| 4,025,472 | 5/1977 | Lepoutre | 260/17.4 |
| 4,051,086 | 9/1977 | Reid | 260/17.4 |

Primary Examiner—Edward M. Woodberry
Attorney, Agent, or Firm—M. Howard Silverstein; David G. McConnell; Curtis P. Ribando

[57] ABSTRACT

Absorbent polymeric compositions are prepared by drying aqueous dispersions of physical mixtures of polyhydroxy polymers, such as starch, with carboxylate-containing synthetic polymers, such as saponified polyacrylonitrile of partially saponified polyacrylamide, and then curing the resulting dry solids with either heat or prolonged standing at room temperature. These compositions typically absorb several hundred times their weight of deionized water.

14 Claims, No Drawings

INCREASING ABSORBENCY OF POLYMERIC COMPOSITIONS BY CURING

BACKGROUND OF THE INVENTION

1. Field of the Invention

This invention relates to the preparation of absorbent polymeric compositions by a procedure simpler and more economical than any heretofore known in the prior art.

2. Description of the Prior Art

Polymeric substances which have the ability to absorb aqueous fluids are known in the prior art. For example, U.S. Pat. Nos. 3,669,103 and 3,810,468 disclose that a variety of monomers may be polymerized, with crosslinking, to give polymeric absorbents. The crosslinking reaction is of critical importance, since the uncrosslinked polymers are water soluble and thus have no utility as absorbents.

Water-absorbing alkali metal salts of saponified granular starch-polyacrylonitrile (PAN) graft copolymers are disclosed in U.S. Pat. No. 3,661,815. In this disclosure, starch is graft polymerized in the granular state, and the saponification is carried out in an alcohol-containing medium to obtain a granular, insoluble material capable of absorbing about 100 times its weight of water. U.S. Pat. No. 3,932,322 discloses a mixture of the composition of U.S. Pat. No. 3,661,815 with fumed silica or alumina. This mixture exhibits an increased rate of fluid uptake and a decreased tendency toward dusting.

Water-absorbing alkali metal salts of saponified gelatinized starch-PAN graft copolymers are disclosed in U.S. Pat. No. 3,997,484, herein incorporated by reference. In this disclosure, starch is gelatinized by heating in water prior to graft polymerization; also, the graft copolymer is saponified in water to give a viscous dispersion of highly swollen but still insoluble microgel particles. Contrary to the absorbent composition of U.S. Pat. No. 3,661,815, the composition of U.S. Pat. No. 3,997,484 may be dried to a continuous film which has an unusually high absorbency for aqueous fluids. Moreover, this film-forming tendency permits a variety of substrates to be coated with thin films of the absorbent composition and thus leads to dramatic increases in fluid absorbencies of the substrates.

SUMMARY OF THE INVENTION

The object of this invention is to prepare insoluble but highly absorbent polymeric compositions from physical mixtures of two or more water-soluble polymers and to prepare these polymeric compositions by simple, economical procedures but not requiring graft polymerization. We have unexpectedly discovered that by drying aqueous dispersions of either physical mixtures of polyhydroxy polymers, such as starch, and carboxylate-containing synthetic polymers, such as saponified PAN, or certain nonabsorbent polyhydroxy-containing graft copolymers, such as saponified starch-polyacrylamide, and then curing the resulting dry solids with either heat or prolonged standing at room temperature, absorbent compositions are obtained which will absorb up to about 1000 times their weight of aqueous fluid. These absorbent compositions are useful for reducing the water content of emulsions and dispersions, for coating substrates to increase their water-holding capacity, for the solidification of liquid wastes, and as thickening agents for aqueous systems.

DETAILED DESCRIPTION OF THE INVENTION

It is well known in the prior art, i.e., U.S. Pat. No. 3,997,484, supra, that when graft copolymers of starch and polyacrylonitrile are saponified with aqueous alkali and the saponified graft copolymer dispersions allowed to dry, the resulting dry polymers will absorb hundreds of times their weight of water without dissolving. This property is unique to the PAN graft copolymers, since physical mixtures of starch and saponified PAN, when allowed to air dry at room temperature, give dry solids, which simply disperse in water without exhibiting any of the useful properties required of a polymeric absorbent. We were therefore surprised to observe that useful absorbent properties could be conferred upon films prepared by air drying starch-saponified PAN physical mixtures by simply heating the films in an oven for a short period of time or by allowing the films to stand at room temperature for several days or a few weeks. For example, when a mixture containing equal weights of unmodified corn starch and PAN was heated in 0.5N sodium hydroxide, dialyzed to remove excess alkali, and dried to a film near room temperature, the resulting film largely dispersed when placed in water and was thus of little use as an absorbent. However, when portions of the film were allowed to stand at room temperature for 12 days, the aged film was largely insoluble when placed in water and absorbed 1038 g. of water per gram of dry film. Similarly, when an aqueous mixture of cooked unmodified corn starch and saponified PAN (containing equal weights of the two components on a dry basis) was dried, a film was obtained which absorbed only 9 g. of water per gram of dry film. However, when a portion of the same film was heated for 30 min. at 110° C., it absorbed 659 times its weight of water. Films prepared from starch in the absence of saponified PAN or from saponified PAN in the absence of starch do not display these properties, and are ineffective as absorbent compositions.

The polyhydroxy polymers may be any starch or starch-containing material including starches and starch-containing flours derived from cereal grains and root crops such as corn, wheat, rice, potato, and tapioca. The amylose and amylopectin components of starch as well as other polyhydroxy polymers such as cellulose and cellulose derivatives may also be used. These polymers may be unmodified, acid modified, enzyme modified, or oxidized. Fibrous cellulose, such as cotton or fluff pulp, or a fabricated cellulose-containing article, such as paper or a woven or nonwoven cloth or textile would be advantageous insofar as absorbent properties could be conferred on these materials by merely applying a solution of the appropriate synthetic polymer, drying, and curing. Polyvinyl alcohol is also a useful polyhydroxy polymer, since the totally synthetic nature of the resultant absorbent greatly retards microorganism attack and biodegradation when the composition is placed in the soil.

If the polyhydroxy polymer is starch or a starch-containing material, it is preferably gelatinized prior to curing. Gelatinization is effected by any known procedure such as heating in the presence of water or an aqueous solution at temperatures of above about 80° C. until the starch granules are sufficiently swollen and disrupted that they form a smooth viscous dispersion in the water. Steam jet cooking at temperatures exceeding about 120° C. is effective for rapid gelatinization.

The carboxylate-containing synthetic polymers useful in the physical mixture include saponified PAN and partially saponified polyacrylamide. Copolymers of acrylamide and sodium acrylate of varying proportions may also be used.

Saponification of the synthetic polymers is carried out in water with any alkali metal hydroxide, preferably sodium hydroxide or potassium hydroxide. It would also be obvious to use ammonium hydroxide, preferably in combination with an alkali metal hydroxide. The preferred mole ratio of alkali to monomer repeating unit in the polymer is in the range of 0.6:1 to 1:1, although mole ratios within the range of about 0.1:1 to 7.2:1 would also cause saponification to take place. Saponifications are preferably carried out in water, although it is obvious that water-containing mixtures, such as ethanol-water, can also be used. The polymer is contacted with the aqueous solution of alkali metal hydroxide from 1 to 3 hours at a temperature of 90°–100° C. Higher temperatures can also be used, if saponifications are run in pressure vessels. Saponification converts the nitrile substituents of PAN to a mixture of carboxamide and alkali metal carboxylate. The amide substituents of the polyacrylamide are also partially converted to alkali metal carboxylates. If desired, the saponification of the synthetic polymer and the gelatinization of the polyhydroxy polymer can be conducted simultaneously after admixture of the two components.

The preparation of the instant absorbent compositions is not limited to two-component mixtures. Mixtures of polyhydroxy polymers as well as mixtures of synthetic polymers would be operable. The polyhydroxy portion and the synthetic portion can also be present as a single component, such as a graft copolymer of a polyhydroxy polymer and a synthetic polymer, which does not otherwise have absorptive properties. Exemplary of such is a saponified starch-polyacrylamide graft copolymer. Unlike the gelatinized starch-saponified PAN of U.S. Pat. No. 3,997,484, supra, when dried to a film near room temperature and placed in water, the saponified starch-polyacrylamide graft copolymer does not behave like an absorbent polymer, but breaks up and becomes dispersed. However, good absorbency properties are obtained upon curing as described below.

Proportions of the polyhydroxy polymer and synthetic polymer components are not critical and are normally in the range of from about 75:25 to about 25:75 parts by weight, and preferably about 50:50. Mixtures outside this range would be expected by those skilled in the art to similarly yield absorbent compositions, although these compositions might show reduced absorbency.

Any conventional method can be used to dry the physical mixtures to water-dispersible dry solids prior to formation of the absorbent compositions. Air drying near room temperature to form a polymeric film has been most frequently used; however, all known methods of drying, such as freeze drying, spray drying, flash drying, or drum drying would be effective. Drying at elevated temperatures, e.g., drum drying, would be preferred, since the drying step and the curing step could be accomplished in one operation. Normally, it is sufficient to dry the material to below about 15–20% moisture content.

The curing of the dried physical mixtures is the critical step in the novel process of forming the instant absorbent compositions. The curing conditions of time and temperature are inversely related to one another; that is, the higher the temperature, the shorter the curing time. The combination of conditions for obtaining optimum absorbency varies with the specific reactants and their proportions, and therefore are not limited to definite values. Normally, the time and temperature are selected to permit the polyhydroxy polymer and the synthetic polymer to sufficiently crosslink or otherwise interact with one another to thereby render the product nondispersible and capable of swelling upon absorption of aqueous fluids. Beyond a certain point in the curing process, the level of absorbency begins to decrease. While not desiring to be bound to any particular theory, this phenomenon is believed to be the result of a reduction in swell-ability of the polymeric composition because of excessive crosslinking. The optimum conditions of curing for a given starting mixture could readily be determined by a person of ordinary skill in the art by measuring the absorbency of product samples taken at periodic intervals of treatment. At room temperature (about 25° C.), optimum absorbency is usually obtained after about 8 days. At elevated temperatures of 110°–150° C., reaction times generally range from about 15–30 min.

An important application for these absorbent polymer compositions is the reduction of the water content of emulsions, suspensions, and dispersions. For example, when a sample of milk containing 11.2% solids was mixed with 1%, by weight, of absorbent and the mixture let stand for 30 min. and then screened to remove water-swollen absorbent polymer, the solids content of the unabsorbed liquid was increased to 13.2%.

Another important application is the coating of various substrates to increase their water-holding capacity. For example when 1%, by weight, of absorbent composition was dried down onto a sample of sand, a 5-g. sample of the coated sand absorbed 4.52 g. of water, as compared with 1.28 g. of water for 5 g. of uncoated sand.

Another application for these absorbent polymers is as thickening agents for aqueous systems. Although films or particles of these absorbent compositions retain their integrity as they swell and imbibe water, it is obvious that a film or particle which has imbibed several hundred times its weight of water will possess little strength and will therefore be easily reduced to a desirably smooth dispersion. The products of the instant invention are thus well suited for use as thickeners. Moreover, since the absorbent polymer compositions swell rapidly but do not actually dissolve, they do not show the undesirable tendency to form surface-hydrated lumps or "gumballs", which is so prevalent in prior art thickeners.

Other uses disclosed in U.S. Pat. No. 3,997,484 for saponified starch-PAN, such as the entrapment and immobilization of enzymes, are anticipated for the absorbent compositions of the instant application. There are also numerous other applications for these absorbents which are not specifically listed but which will be obvious to those skilled in the art.

The following examples are intended only to further illustrate the invention and are not intended to limit the scope of the invention which is defined by the claims.

EXAMPLE 1

Corn Starch-PAN

A. An Erlenmeyer flask was charged with 0.50 g. of unmodified corn starch, 0.50 g. of polyacrylonitrile (having an intrinsic viscosity of 3.7 in dimethylformamide at 25° C.), and 20 ml. of 0.5N sodium hydroxide. The mixture was heated on a steam bath for about 20 min. and then placed in a 95°–100° C. oven for 2 hours. The reaction mixture was diluted with 400 ml. of water and exhaustively dialyzed against distilled water. The dialyzed dispersion, which contained 0.144% solids, had a pH of 6.0, and showed a Brookfield viscosity of 89 cp. at 30 r.p.m. and 25° C. The dispersion was poured onto a "Teflon"-coated tray and allowed to dry to a film in a forced air oven at 35°–40° C.

B. A section of the film from Example 1A was placed in distilled water and allowed to stand for about 1 hour. The film dispersed and seemed to largely dissolve, and it was thus of little use as an absorbent polymer.

C. The film from Example 1A was allowed to stand at room temperature for 12 days. Absorbency was then tested by adding 4.0 mg. of film to 50 ml. of distilled water. After 30 min., the swollen polymer was separated from excess water by screening through a tared 280-mesh sieve which was 4.8 cm. in diameter. The polymer on the sieve was allowed to drain for 20 min., and the sieve was weighed to determine the weight of water-swollen gel (4.15 g.). An absorbency of 1038 g. of water per gram of polymer was calculated (Table 1).

A 64.4-mg. portion of 12-day-old film was added to 50 ml. of a synthetic urine solution prepared from 0.64 g. of $CaCl_2$, 1.14 g. of $MgSO_4 \cdot 7H_2O$, 8.20 g. of NaCl, 20.0 g. of urea, and 1000 ml. of water. The mixture was allowed to stand for 30 min., screened through the 280-mesh sieve, and allowed to drain for 20 min. A synthetic urine absorbency of 27 g. per gram of polymer was calculated from the 1.81 g. of swollen polymer retained on the sieve (Table 1).

D. Portions of 13-day-old film from Example 1A were heated in a forced air oven for either 15 min. at 110° C., 15 min. at 150° C., or 30 min. at 150° C., and absorbency tests were run as in Example 1C. Results are given in Table 1.

E. The film from Example 1A was allowed to stand at room temperature for 61 days. The absorbency was 875 g. of water per gram of polymer, as determined by the method of Example 1C (Table 1).

EXAMPLE 2

Corn starch-PAN

An Erlenmeyer flask was charged with 0.50 g. of polyacrylonitrile (same used in Example 1A) and 20 ml. of 0.5N NaOH, and the mixture was heated and dialyzed as in Example 1A. The dialyzed dispersion contained 0.109% solids and had a pH of 6.5. A suspension of 2.2 g. of unmodified corn starch in 1 l. of water was passed through a steam jet cooker at 121° C. to give a starch dispersion containing 0.117% solids. A 465-ml. portion of this starch dispersion was mixed with 500 ml. of the saponified polyacrylonitrile dispersion to give a final dispersion containing equal weights of the two polymers. This mixture was poured onto a "Teflon"-coated tray and allowed to dry to a film in a forced air oven at 35°–40° C. A section of film which had stood at room temperature for 4 days showed an absorbency of only 9 g. of water per gram of polymer, when tested by the method of Example 1C. When the film was heated, the absorbencies given in Table 2 were obtained.

A portion of the film which had been heated for 30 min. at 150° C. was placed in 0.1N sodium hydroxide and heated for 1 hr. at 98° C. The film swelled but did not dissolve.

EXAMPLE 3

Control-Starch

An Erlenmeyer flask was charged with 1.00 g. of unmodified corn starch and 20 ml. of 0.5N sodium hydroxide, and the mixture was heated and dialyzed as in Example 1A. The pH of the dialyzed dispersion was adjusted to 7.1 with 0.1M sodium hydroxide and the dispersion poured onto a "Teflon"-coated tray and allowed to dry to a film in a forced air oven at 35°–40° C. A section of film which had stood at room temperature for 5 days showed an absorbency of 18 g. of water per gram of polymer. A section of film which had stood at room temperature for 96 days showed a water absorbancy of only 19 g./g.

Table 1

|  | $H_2O$ absorbency | Syn. urine absorbency |
|---|---|---|
| No treatment | — | — |
| 12 days room temperature | 1038 | 27 |
| 61 days room temperature | 875 | — |
| 15 min. at 110° C.[a] | 854 | 24 |
| 15 min. at 150° C.[a] | 180 | 24 |
| 30 min. at 150° C.[a] | 102 | 17 |

[a]After standing for 13 days at room temperature.

Table 2

|  | $H_2O$ absorbency | Syn. urine absorbency |
|---|---|---|
| 15 min. at 110° C. | 103 | 10 |
| 30 min. at 110° C. | 659 | 19 |
| 15 min. at 150° C. | 208 | 16 |
| 30 min. at 150° C. | 76 | 15 |

When a section of the 96-day-old film was heated in a forced air oven for 15 min. at 150° C., its water absorbency was only 20 g./g.

EXAMPLE 4

Control-PAN

A graft copolymer of starch and polyacrylonitrile was prepared by allowing unmodified corn starch (preswollen in water at 60° C.) to react with acrylonitrile in the presence of ceric ammonium nitrate. After removal of homopolymer, the graft copolymer contained 57% by weight of acrylonitrile. The starch portion of the graft copolymer was removed by hydrolysis in 0.5N hydrochloric acid. The remaining granules of polyacrylonitrile, essentially free of carbohydrate, had an intrinsic viscosity of 3.3 in dimethylformamide at 25° C. An Erlenmeyer flask was charged with 0.57 g. of this polyacrylonitrile and 20 ml. of 0.5N sodium hydroxide, and the mixture was heated and dialyzed as in Example 1A. The dialyzed dispersion (pH 6.4) was poured onto a "Teflon"-coated tray and allowed to dry to a film in a forced air oven at 35°–40° C. The film did not behave like an absorbent polymer but totally dispersed when placed in water. A similar behavior was observed after the film had stood at room temperature for 167 days. Moreover, heating the aged film in a forced air oven for 1 hour at 150° C. did not change its properties.

EXAMPLE 5

Corn starch-poly(acrylamide-co-acrylic acid)

A poly(acrylamide-co-acrylic acid) polymer was prepared by dissolving 0.03 mole each of acrylamide and acrylic acid in 80 ml. of water and irradiating the solution with cobalt-60 to a total dose of 0.1 Mrad. The reaction mixture was dialyzed, neutralized with sodium hydroxide to pH 7.1, and freeze dried. The conversion of monomers to polymer was about 85%. A solution of 0.50 g. of poly(acrylamide-co-acrylic acid) in 200 ml. of water was prepared. In a separate flask, 0.50 g. (dry basis) of an acid-modified corn starch of approximately 90 fluidity was added to 200 ml. of water and the mixture heated to 99° C. and then cooled back to room temperature. The two polymer solutions were mixed thoroughly and then poured onto a "Teflon"-coated tray and allowed to dry to a film in a forced air oven at 35°–40° C. The film did not behave like an absorbent polymer but dispersed when placed in water. When the film was heated, the absorbencies given in Table 3 were obtained. The method of Example 1C was used to obtain absorbency.

EXAMPLE 6

50% Wheat starch-50% polyacrylamide

A solution of 0.50 g. of a commercial anionic polyacrylamide (containing 12.8 mole percent sodium acrylate and 2.5 mole percent acrylic acid repeating units) in 78 ml. of water was prepared, and sufficient 0.116N sodium hydroxide (21.6 ml.) was added to produce a total of 50 mole percent sodium acrylate, assuming that the alkali would be totally utilized for saponification. The solution was heated to 100° C. over about a 15-min. period and was then allowed to stir and cool to 35°–40° C. over a period of about 1 hour. The pH of the solution was 11.1 Pregelatinized wheat starch (0.50 g.) was then added and the mixture again heated to 100° C. and allowed to cool. The reaction mixture was diluted with 100 ml. of water, dialyzed, and the pH of the dialyzed dispersion adjusted to 8.4 with 0.1N sodium hydroxide. The dispersion was poured onto a "Teflon" tray and allowed to dry to a film in a forced air oven at 35°–40° C. When placed in water, the film imbibed water with very little swelling. When the film was heated, the absorbencies given in Table 4 were obtained (method of Example 1C).

EXAMPLE 7

25% Wheat starch-75% polyacrylamide

A solution of 0.75 g. of the anionic polyacrylamide used in Example 6 in 117 ml. of water was prepared and 32.4 ml. of 0.116N sodium hydroxide added (sufficient alkali to theoretically give 50% saponification). The mixture was heated to 100° C. and allowed to cool as in Example 6. Pregelatinized wheat starch (0.25 g.) was added, and the mixture again heated to 100° C. and allowed to cool. The mixture was diluted with 50 ml. of water, dialyzed, and the pH adjusted to 8.3. The resulting dispersion was then dried to a film as in Example 6. Water absorbencies of the film (method of Example 1C) are given in Table 5.

EXAMPLE 8

75% Wheat starch-25% polyacrylamide

A solution of 0.25 g. of the anionic polyacrylamide used in Example 6 in 39 ml. of water was prepared, and 10.8 ml. of 0.116N sodium hydroxide added (sufficient alkali to theoretically give 50% saponification). The mixture was heated to 100° C. and allowed to cool as in Example 6, and 50 ml. of water was then added.

Table 3

|  | $H_2O$ absorbency |
|---|---|
| 15 min. at 110° C. | 6 |
| 30 min. at 110° C. | 7 |
| 15 min. at 150° C. | 136 |
| 30 min. at 150° C. | 87 |

Table 4

|  | $H_2O$ absorbency |
|---|---|
| 30 min. at 110° C. | 32 |
| 15 min. at 150° C. | 207 |
| 30 min. at 150° C. | 229 |

Table 5

|  | $H_2O$ absorbency |
|---|---|
| Not heated | 2 |
| 15 min. at 150° C. | 138 |
| 30 min. at 150° C. | 163 |

Pregelatinized wheat starch (0.75 g.) was added, and the mixture again heated to 100° C. and allowed to cool. The mixture was diluted with 100 ml. of water, dialyzed, and the pH adjusted to 8.3. The resulting dispersion was then dried to a film as in Example 6. Water absorbencies of the film (method of Example 1C) are given in Table 6.

EXAMPLE 9

Wheat starch-polyacrylamide (excess alkali)

A solution of 0.50 g. of the anionic polyacrylamide used in Example 6 in 73 ml. of water was prepared, and 27 ml. of 0.5N sodium hydroxide added (twice the amount of alkali theoretically needed to give 100% saponification). The mixture was heated to 100° C. and allowed to cool as in Example 6 to give a solution with a pH of 11.9. Pregelatinized wheat starch (0.50 g.) was added, and the mixture again heated to 100° C. and allowed to cool. The mixture was diluted with 100 ml. of water, dialyzed, and the pH adjusted to 8.3. The resulting dispersion was then dried to a film as in Example 6. Water absorbencies of the film (method of Example 1C) are given in Table 7. Infrared analysis of the film showed sodium carboxylate absorption but no detectable carbonyl absorption due to carboxylic acid.

EXAMPLE 10

Wheat starch-anionic polyacrylamide (no further saponification)

A solution of 0.50 g. of the anionic polyacrylamide used in Example 6 in 100 ml. of water was prepared. In a separate flask, 0.50 g. of pregelatinized wheat starch was suspended in 100 ml. of water and 0.5N sodium hydroxide added to give a pH of 11.1. The starch slurry was heated to 100° C., was allowed to cool as in Example 6, and was then mixed with the solution of anionic polyacrylamide. The combined mixture was dialyzed and the pH adjusted to 8.4. The dispersion was finally dried to a film as in Example 6. Water absorbencies of the film (method of Example 1C) are given in Table 8.

EXAMPLE 11

Control-polyacrylamide

A solution of 0.75 g. of the anionic polyacrylamide used in Example 6 in 117 ml. of water was prepared and 32.4 ml. of 0.116N sodium hydroxide added (sufficient alkali to theoretically give 50% saponification). The mixture was heated to 100° C. and allowed to cool as in Example 6, and the heating and cooling cycle was then repeated a second time. The mixture was diluted with 50 ml. of water, dialyzed, and the pH adjusted to 8.3. The resulting dispersion was then dried to a film as in Example 6. The film dissolved when placed in water and was thus of no use as an absorbent polymer. When the film was heated for either 15 min. or 30 min. at 150° C., it also dissolved.

EXAMPLE 12

Control-wheat starch

A suspension of 0.75 g. of pregelatinized wheat starch in 100 ml. of water was prepared, and the pH was adjusted to 11.0 with 0.1N sodium hydroxide. The mixture was heated to 100° C. and allowed to cool as in Example 6. The mixture was then diluted with 100 ml. of water, dialyzed, and the pH adjusted to 8.3. The resulting dispersion was then dried to a film as in Example 6.

Table 6

|  | $H_2O$ absorbency |
|---|---|
| Not heated | 16 |
| 15 min. at 150° C. | 29 |
| 30 min. at 150° C. | 34 |

Table 7

|  | $H_2O$ absorbency |
|---|---|
| Not heated | 11 |
| 15 min. at 150° C. | 199 |
| 30 min. at 150° C. | 166 |

Table 8

|  | $H_2O$ absorbency |
|---|---|
| Not heated | 20 |
| 15 min. at 150° C. | 86 |
| 30 min. at 150° C. | 54 |

When the absorbancy was tested by the method of Example 1C, the film absorbed only 9 g. of water per gram of polymer. The absorbency dropped to 4 after heating the film for 15 min. at 150° C.

EXAMPLE 13

PVA (99% hydrolyzed)-PAN

An Erlenmeyer flask was charged with 0.50 g. of a commercial polyvinyl alcohol (99% hydrolyzed), 0.50 g. of the polyacrylonitrile used in Example 1A, and 20 ml. of 0.5N sodium hydroxide. The resulting mixture was heated and then dialyzed as in Example 1A. The pH of the dialyzed dispersion was adjusted to 7.2 with dilute sodium hydroxide, and the resulting dispersion was freeze dried. Water absorbencies of the freeze dried solid (method of Example 1C) are given in Table 9.

EXAMPLE 14

PVA (85% hydrolyzed)-PAN

The procedure of Example 13 was repeated, with the exception that the commercial polyvinyl alcohol had a degree of hydrolysis of about 85%. Water absorbencies of the freeze dried solid are given in Table 9.

EXAMPLE 15

Corn starch-polyacrylamide graft copolymer

A starch-polyacrylamide graft copolymer was prepared by allowing 32.4 g. of unmodified corn starch, preirradiated with cobalt-60 to a total dose of 1 Mrad, to react with 50 g. of acrylamide in 283 ml. of water. The yield of graft copolymer, containing 53.4% by weight of polyacrylamide, was 70 g.

Table 9

| Example | Polyvinyl alcohol used | Product treatment[a] | $H_2O$ absorbency |
|---|---|---|---|
| 13 | 99% Hydrol. | Not heated | 111 |
|  |  | 15 min. at 150° C. | 183 |
|  |  | 30 min. at 150° C. | 133 |
| 14 | 85% Hydrol. | Not heated | 116 |
|  |  | 15 min. at 150° C. | 153 |
|  |  | 30 min. at 150° c. | 114 |

[a]After standing for 8 days at room temperature.

An Erlenmeyer flask was charged with 1.00 g. of the starch-polyacrylamide graft copolymer and 20 ml. of 0.5N sodium hydroxide, and the mixture was heated, dialyzed, and dried to a film as in Example 1A. The film did not behave as an absorbent polymer, even after standing at room temperature for 97 days, but broke up and largely dispersed when it was placed in water. However, when a portion of the film was heated in a forced air oven for 30 min. at 110° C., it was an excellent absorbent and absorbed over 2200 g. of water and 44 g. of synthetic urine per gram of polymer. When a portion of the film was heated for 15 min. at 150° C., it absorbed 154 g. of water and 30 g. of synthetic urine per gram of polymer.

EXAMPLE 16

This example illustrates the utility of the instant absorbent compositions as thickening agents for aqueous systems.

A smooth 1% dispersion of the absorbent composition of Example 1E was prepared by adding 0.10 g. of absorbent composition to 10 ml. of water and stirring the misture gently with a spatula. Brookfield viscosity of the dispersion (25° C.) was 1250 cp. at 12 r.p.m. and 920 cp. at 30 r.p.m.

EXAMPLE 17

This example shows the utility of the instant absorbent compositions for the coating of various substrates to increase their water-holding capacity.

A dispersion of 0.10 g. of the absorbent composition of Example 1E in 10 ml. of water was prepared, and 10 g. of sand was mixed in. The resulting mixture was allowed to air dry. A 5.0-g. portion of the coated sand was weighed into a small beaker, and deionized water was added until no more water was absorbed. The amount of water absorbed by the coated sand was 4.52 g. as compared with 1.28 g. of water for a 5.0-g. sample of uncoated sand.

EXAMPLE 18

This example shows the utility of the instant absorbent polymers for concentrating aqueous emulsions or dispersions.

A 10-ml. sample of milk containing 11.2% solids was mixed with 0.10 g. of the absorbent polymer composition of Example 1E and the mixture allowed to stand for 30 min. Unabsorbed liquid was separated by screening through a 280-mesh sieve. The unabsorbed liquid containing 13.2% solids.

We claim:

1. A method for producing absorbent polymeric compositions comprising the following steps:
   a. providing an aqueous dispersion of a physical mixture of a polyhydroxy polymer and a carboxylate-containing synthetic polymer, wherein said synthetic polymer is characterized by the property of remaining water dispersible upon initial drying of the aqueous dispersion of said physical mixture;
   b. drying said aqueous dispersion to form water-dispersible dry solids of said polyhydroxy polymer and said synthetic polymer; and
   c. curing said dry solids by treatment with a combination of time and temperature sufficient to render said solids nondispersible and capable of swelling upon absorption of aqueous fluids.

2. The method as described in claim 1 wherein said polyhydroxy polymer is selected from the group consisting of starches, starch-containing flours, amylose, amylopectin, cellulose, cellulose derivatives, and polyvinyl alcohol.

3. The method as described in claim 1 wherein said polyhydroxy polymer is selected from the group consisting of cereal grain starches, cereal grain flours, root crop starches, and root crop flours.

4. The method as described in claim 3 wherein said polyhydroxy polymer is gelatinized.

5. The method as described in claim 1 wherein said carboxylate-containing synthetic polymer is selected from the group consisting of saponified polyacrylonitrile, saponified polyacrylamide, and copolymers of acrylamide and sodium acrylate.

6. The method as described in claim 1 wherein the proportion of polyhydroxy polymer to synthetic polymer is in the range of about 75:25 to about 25:75 parts by weight.

7. The method as described in claim 1 wherein the proportion of polyhydroxy polymer to synthetic polymer is about 50:50 parts by weight.

8. The method as described in claim 1 wherein said curing is at room temperature for a time of at least about 8 days.

9. The method as described in claim 1 wherein said curing is at an elevated temperature in the range of about 110°–150° C. for a time of about 15–30 min.

10. Absorbent polymeric compositions produced by the process of claim 1.

11. A method for producing absorbent polymeric compositions comprising the following steps:
    a. providing an aqueous dispersion of a graft copolymer of a polyhydroxy polymer and a carboxylate-containing synthetic polymer, wherein said graft copolymer is characterized by the property of remaining water dispersible upon initial drying of the aqueous dispersion thereof;
    b. drying said aqueous dispersion to form water-dispersible dry solids of said graft copolymer;
    c. curing said dry solids by treatment with a combination of time and temperature sufficient to render said solids nondispersible and capable of swelling upon absorption of aqueous fluids.

12. The method as described in claim 11 wherein said polyhydroxy polymer is a gelatinized starch or gelatinized starch-containing flour and said carboxylate-containing synthetic polymer is saponified polyacrylamide or a copolymer of acrylamide and sodium acrylate.

13. The method as described in claim 11 wherein said curing is at room temperature for a time of at least about 8 days.

14. The method as described in claim 11 wherein said curing is at an elevated temperature in the range of about 110°–150° C. for a time of about 15–30 minutes.

* * * * *